(12) United States Patent
Francis et al.

(10) Patent No.: US 7,927,586 B2
(45) Date of Patent: Apr. 19, 2011

(54) **VACCINE FOR PORCINE POST-WEANING DIARRHEA CAUSED BY ENTEROTOXIGENIC *ESCHERICHIA COLI***

(75) Inventors: David Francis, Brookings, SD (US); Weiping Zhang, Brookings, SD (US)

(73) Assignee: South Dakota State University, Brookings, SD (US)

( * ) Notice: Subject to any disclaimer, the term of this patent is extended or adjusted under 35 U.S.C. 154(b) by 0 days.

(21) Appl. No.: 12/169,259

(22) Filed: Jul. 8, 2008

(65) Prior Publication Data

US 2010/0008949 A1    Jan. 14, 2010

(51) Int. Cl.
*A61K 39/108* (2006.01)
(52) U.S. Cl. .................................. 424/93.2; 435/252.33
(58) Field of Classification Search .................. None
See application file for complete search history.

(56) References Cited

U.S. PATENT DOCUMENTS

| | | | |
|---|---|---|---|
| 4,053,584 A | 10/1977 | Dobrescu et al. | |
| 4,157,390 A | 6/1979 | Parry et al. | |
| 4,237,115 A | 12/1980 | Brinton, Jr. | |
| 4,761,372 A * | 8/1988 | Maas et al. ................. | 424/200.1 |
| 5,891,860 A | 4/1999 | Heerze et al. | |
| 6,019,982 A | 2/2000 | Clements et al. | |
| 6,033,673 A | 3/2000 | Clements | |
| 6,069,137 A | 5/2000 | Heerze et al. | |
| 6,200,576 B1 | 3/2001 | Hwong et al. | |
| 6,217,883 B1 | 4/2001 | Allan et al. | |
| 6,296,855 B1 | 10/2001 | Hemmen et al. | |
| 6,310,043 B1 | 10/2001 | Bundle et al. | |
| 6,436,407 B1 | 8/2002 | Clements et al. | |
| 6,440,423 B1 | 8/2002 | Clements et al. | |
| 7,063,852 B2 | 6/2006 | Clements | |
| 7,163,820 B1 | 1/2007 | Nagy et al. | |
| 7,291,342 B2 | 11/2007 | Melson et al. | |
| 2002/0146431 A1 | 10/2002 | Allan et al. | |

OTHER PUBLICATIONS

Dubreuil et al. Microbiology (1997), 143, 1783-1795.*
Dewey et al., "The Impact of Disease on Nursery Pig Production," Workshop # 7, Amer. Assoc. Swine Practitioners, Indianapolis, pp. 3-11, 2000.
Francis, Ph.D., "Enterotoxigenic *Escherichia coli* infection in pigs and its diagnosis," J. Swine Health Prod. 10, pp. 171-175, 2000.
Francis, PhD., et al. "Evaluation of a live avirulent *Escherichia coli* vaccine for K88+, LT+ enterotoxigenic colibacillosis in weaned pigs," Am. J. Vet. Res., vol. 52, pp. 1051-1055, 1991.
Francis et al., "Expression of Mucin-Type Glycoprotein K88 Receptors Strongly Correlates with Piglet Susceptabilty to K88+ Enterotoxigenic *Escherichia coli*, but Adhesion of This Bacterium to Brush Borders Does Not," Infect. Immun, vol. 66, pp. 4050-4055, Sep. 1998.
Frantz et al., "Production and Testing of *Escherichia coli* (LTb) Toxoid," pp. 500-517, In: Acres S. (ed.), Fourth International Symposium on Neonatal Diarrhea. Saskatoon, Saskatchewan, CA., 1983.
Frydendahl, "Prevalence of serogroups and virulence genes in *Escherichia coli* associated with post weaning diarrhoea and edema disease in pigs and a comparison of diagnostic approaches," Vet. Microbiol., vol. 85, pp. 169-182, 2002.
Hampson, "Postweaning *Escherichia coli* Diarrhoea in Pigs," pp. 171-191 in C.L. Gyle (ed.) *Escherichia coli* in domestic animals and human., CAB Internatioanl, Oxon, UK, 1994.
Tubbs et al. "Reweaning Morbidity and Mortality in the United States Swine Herd," Swine Health Prod., vol. 1, pp. 21-38, 1993.
Zhang et al. "Significance of Heat-Stable and Heat-Labile Enterotoxins in Porcine Colibacillosis in an Additive Model for Pathogenicity Studies,"Infect. Immun., vol. 74(6), pp. 3107-3114, Jun. 2006.
Berberov et al., "Relative Importance of Heat-Labile Enterotoxin in the Severe Diarraheal Disease in the Gnotobiotic Piglet Model by a Strain of Enterotoxigenic *Escherichia coli* That Produces Multiple Enterotoxins,"Infect. Immun., vol. 72(7), pp. 3914-3924, Jul. 2004.
Friendship, "Swine Research at Guelph: Exploring alternatives to Antibiotics," Abstract and Introduction, London Swine Conference, Conquering the Challenges, Apr. 11-12, 2002, 1 pg.
Zhang et al., Prevalence of virulence genes in *Escherichia coli* strains recently isolated from young pigs with diarrhea in the US, Vet. Microbiol., vol. 123, pp. 145-152, 2007.

\* cited by examiner

*Primary Examiner* — N. M Minnifield
*Assistant Examiner* — Brian J Gangle
(74) *Attorney, Agent, or Firm* — Lane & Waterman LLP

(57) ABSTRACT

Vaccines and methods for making and using the same. An example vaccine may be a vaccine against enterotoxigenic *Escherichia coli*. The vaccine may include an *Escherichia coli* strain. The *Escherichia coli* strain may produce K88 fimbria and a fusion protein including a mutant LT enterotoxin linked with a STb enterotoxin. An example method for producing a vaccine for porcine post-weaning diarrhea may include providing a first strain of *Escherichia coli*. The strain may include the eltAB gene and the estB gene. The method may also include amplifying the eltAB gene, mutating the eltAB gene, generating a genetic fusion of the mutant eltAB gene with the estB gene, and transforming a second strain of *Escherichia coli* with the genetic fusion.

2 Claims, No Drawings

VACCINE FOR PORCINE POST-WEANING DIARRHEA CAUSED BY ENTEROTOXIGENIC *ESCHERICHIA COLI*

FIELD OF THE INVENTION

The present invention pertains to vaccines. More particularly, the present invention pertains to vaccines for post-weaning diarrhea caused by enterotoxigenic *Escherichia coli* (ETEC) in pigs.

BACKGROUND

*Escherichia coli* (*E. coli*) is a common species of bacteria that is notorious for, among other things, causing intestinal problems including diarrhea. One class of *E. coli* that is associated with intestinal disease and/or diarrhea is the so-called enterotoxigenic *E. coli* (ETEC). ETEC are probably best known for causing traveler's diarrhea. Contamination of the food and/or water supply are typically the source of ETEC.

The disease caused by ETEC is the result of both the adhesion of the bacteria to the intestinal wall and the release of toxins (e.g., enterotoxins) into the system of the host. Adhesion to the intestinal wall is accomplished through one or more "fimbriae" (i.e., appendages) that are disposed on the exterior of the bacteria and allow it adhere. The fimbriae of a particular ETEC strain tend to be host-specific. For example, the ETEC that infect pigs carry K-88 fimbriae whereas strains that infect humans carry CFA I and CFA II fimbriae.

ETEC produce two toxins: the heat-labile "LT" toxin and the heat-stable "ST" toxin. The LT toxin includes an active or "A" subunit and five binding or "B" subunits. LT acts in a manner similar to cholera toxin in that it increases the level of cAMP in intestinal cells, and this causes an increase in electrolyte and water excretion (diarrhea). The ST toxin may be "type a" (i.e., STa) or "type b" (i.e., STb). ST stimulates production of cGMP, also leading to increased fluid excretion and diarrhea. Because enterotoxigenic *E. coli* strains are non-invasive, they do not cause inflammation, bloody diarrhea, or systemic symptoms such as fever.

In the North American (and World-Wide) swine industry, neonatal and post-weaning diarrhea caused by ETEC is one of the most economically important porcine diseases. For example, ETEC strains are believed to be responsible for the death of 10.8% of all pre-weaned pigs and up to more than 3% of all weaned pigs. (Tubb et al., 1993, Preweaning morbidity and mortality in the United States swine heed, Swine Health Prod. 1:21-28; Hampson, 1994, Postweaning *Escherichia coli* diarrhea in pigs, pp 171-191 in ed. C. L. Gyle, *Escherichia coli* in domestic animals and humans, CAB International, Oxon, UK; Dewey et al., 2000, The impact of disease on nursery pig production, Amer. Assoc. Swine Practictioners, P 3-11, Indianapolis; the entire disclosures of which are all incorporated herein by reference). There is an ongoing need for ways to treat and/or prevent neonatal and post-weaning diarrhea in pigs.

BRIEF SUMMARY

The invention provides design, material, manufacturing method, and use alternatives for vaccines. An example vaccine may be a vaccine against enterotoxigenic *Escherichia coli*. The vaccine may include an *Escherichia coli* strain. The *Escherichia coli* strain may produce K88 fimbria and a fusion protein including a mutant LT enterotoxin linked with a STb enterotoxin.

An example method for producing a vaccine for porcine post-weaning diarrhea may include providing a first strain of *Escherichia coli*. The strain may include the eltAB gene and the estB gene. The method may also include amplifying the eltAB gene, mutating the eltAB gene, generating a genetic fusion of the mutant eltAB gene with the estB gene, and transforming a second strain of *Escherichia coli* with the genetic fusion.

Another example vaccine may be a live vaccine for porcine post-weaning diarrhea. The vaccine may include an *Escherichia coli* strain. The *Escherichia coli* strain may produce K88 fimbria and a fusion protein including a mutant LT enterotoxin linked with a STb enterotoxin.

The above summary of some embodiments is not intended to describe each disclosed embodiment or every implementation of the present invention. The Figures, and Detailed Description, which follow, more particularly exemplify these embodiments.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Example vaccines are described herein that may be designed to be effective for the prevention of diarrhea caused by enterotoxigenic *Escherichia coli* (ETEC). The vaccine may be effective for the prevention of post-weaning diarrhea caused by ETEC in pigs. Other vaccines are contemplated, which may be designed with the same or similar design considerations, that may be effective for the prevention of diarrhea cause by ETEC in other mammals including humans. Additionally, the vaccines may be designed so that they are easy and safe to produce and so that essentially anyone raising, handling, transporting, breeding, or otherwise working with pigs can use the vaccine to protect against post-weaning diarrhea in pigs.

The vaccine may be designed so that it may be delivered to pigs in a convenient manner. For example, the vaccine may be administered to pigs orally through the food supply (e.g., with feed, milk or milk replacer, and/or water). This route of administration may be desirable, for example, because it may minimize the amount of handling that the pigs are subjected to. Alternatively, the vaccine may be administered in other suitable manner including parenterally, intravenously, intramuscularly, topically, or subcutaneously. Of course, the route of administration may be dictated or otherwise determined by the form of the vaccine.

The design of the vaccine may take into account the key virulence factors of ETEC in porcine diarrhea, which may include: 1) bacterial adhesions which mediate the attachment of bacteria to the surface of host enterocytes and initiate colonization; and 2) enterotoxins which are responsible for fluid secretion. For example, recent studies have shown that over 50-70% of *E. coli* strains implicated in post-weaning diarrhea produce the K88 type of fimbria. Of the K88 fimbria, K88ac is the only K88 variant that has been found in North America, and is by far the most common in the world. The K88ac fimbriae have also be established as an essential virulence determinant in porcine ETEC colibacillosis (see, for example, Francis et al., 1998, Expression of muncin-type glycoprotein K88 receptors strongly correlates with piglet susceptibility to K88+ enterotoxigenic *Escherichia coli*, but adhesions of this bacterium to brush borders does not, Infect. Immun. 66, 4050-4055, the entire disclosure of which is herein incorporated by reference). Thus, a vaccine that targets K88 fimbria, and/or K88ac fimbria, as an antigen may be desirable.

All K88+ strains produce LT and STb (see, for example, Francis, D. H., 2002, Enterotoxigenic *Escherichia coli* infection in pigs and its diagnosis, J. Swine Health Prod. 10, 171-175; Frydendahl, K., 2002, Prevalence of serogroups and virulence genes in *Escherichia coli* associated with postweaning diarrhea and edema disease in pigs and a comparison of diagnostic approaches, Vet. Microbiol. 85, 169-182; and Zhang et al., 2007, Prevalence of virulence genes in *Escherichia coli* strains isolated from young pigs with diarrhea in North Central U.S., Vet. Microbiol. 123, 145-152; the entire disclosures of which are all herein incorporated by reference). Essentially all *E. coli* strains implicated in post-weaning diarrhea produce STb. Several studies have also demonstrated that LT and STb enterotoxin are responsible for the diarrhea associated with ETEC infection (see, for example, Berberov et al., 2004, Relative importance of heat-labile enterotoxin in the causation of severe diarrheal disease in the gnotobiotic piglet model by a strain of entertoxigenic *Escherichia coli* that produces multiple enterotoxins, Infect. Immun. 72, 3914-3924 and Zhang et al., 2006, Significance of heat-stabile and heat-labile enterotoxins in porcine colibacillosis in an additive model for pathogenicity studies, Infect. Immun. 74, 3107-3114; the entire disclosures of which are all herein incorporated by reference). Thus, a vaccine that targets LT and/or STb as an antigen may be desirable. Furthermore, a vaccine that contained antigens to K88ac, LT, and STb may be desirable because it would cover all essential virulence determinants of a major swine pathogen. The uniqueness of vaccines utilizing this design strategy is that a vaccine can be produced that expresses antigens of all the major virulence factors of ETEC. At least some of these vaccines appear to be substantially avirulent in piglets.

An additional unique aspect of the vaccines described herein is that the vaccines may function as a competitive exclusion probiotic as well as a vaccine (e.g., in at least some embodiments, the vaccines described herein may have probiotic efficacy). A competitive exclusion probiotic in a microbial organism competes with a pathogen for the biological niche within the host required by the pathogen to cause disease. The great benefit of a dual purpose probiotic/vaccine strain is that the protection from the disease can occur in short order critical in the swine industry where pigs may change ownership at weaning, with vulnerability to ETEC disease occurring shortly after. Further, because the organism may be a live vaccine, it can be delivered in the nursery watering system and does not require individual animal handling, an issue of concern to the swine industry.

Vaccines

In at least some embodiments, the vaccines described herein are live vaccines that are designed to protect young pigs from diarrhea disease caused by enterotoxigenic *E. coli* strains. The vaccines may comprise a live strain of *E. coli* that expresses antigens from K88ac fimbria and a genetically engineered fusion protein. The fusion protein may include a mutant and/or non-toxic heat-labile (LT) enterotoxin and a heat-stabile type B (STb) enterotoxin.

In other embodiments, the vaccine may comprise a live strain of *E. coli* that expresses antigens from K88ac fimbria and a mutant and/or non-toxic heat-labile (LT) enterotoxin.

In still other embodiments, the vaccine may comprise a live strain of *E. coli* that expresses antigens from K88ac fimbria and a mutant and/or non-toxic heat-stabile type B (STb) enterotoxin.

In still other embodiments, the vaccine may comprise a live strain of *E. coli* that produces a mutant and/or non-toxic heat-labile (LT) enterotoxin, a non-toxic heat-stabile type B (STb) enterotoxin, or both, for example joined as a fusion protein.

In still other embodiments, the vaccine may comprise a live strain of *E. coli* that expresses antigens for fimbria other than K88ac, for example other fimbria associated with ETEC. These vaccines may also express a mutant and/or non-toxic heat-labile (LT) enterotoxin, a mutant and/or non-toxic heat-stabile type B (STb) enterotoxin, or both.

The vaccines described herein may be delivered to pigs by inoculating the food supply for the pigs. For example, the vaccine may be added to the feed, the milk (or milk replacer), the water, or both for the pigs.

The vaccines described herein may be manufactured and/or produced by providing a first strain of *Escherichia coli* that includes the eltAB gene and the estB gene, amplifying the eltAB gene, mutating the eltAB gene, generating a genetic fusion of the mutant eltAB gene with the estB gene, and transforming a second strain of *Escherichia coli* with the genetic fusion.

EXAMPLES

The invention may be further clarified by reference to the following Examples, which serve to exemplify some of the preferred embodiments, and not to limit the invention in any way.

Example 1

Isolation and Cloning of the eltAB Gene

The source used for the eltAB gene (which codes the LT enterotoxin) and the estB gene (which codes the STb enterotoxin) was total genomic DNA from a porcine enterotoxigenic *Escherichia coli* (ETEC) field isolate designated "field isolate 3030-2". Field isolate 3030-2 was deposited on Jun. 6, 2008 under the terms of the Budapest Treaty with the American Type Culture Collection, 10801 University Blvd., Manassas, Va. 20110-2209, USA (ATCC®) and was given ATCC Patent Deposit Designation PTA-9262. All restrictions on the availability to the public of the deposited material will be irrevocably removed upon the granting of the patent, except for the requirements specified in 37 C.F.R. §1.808(b), and the term of the deposit will comply with 37 C.F.R. §1.806.

Genomic DNA was isolated from field isolate 3030-2 using DNeasy® Tissue kit (commercially available from company QIAGEN, CA). The resultant isolated genomic DNA was kept/diluted to a 0.1 μg/μl stock solution. This stock solution was used as the DNA source and/or template for amplifying the eltAB (coding the LT enterotoxin) gene and the estB (coding the STb enterotoxin) gene. The eltAB gene is composed of a nucleotide sequence represented by SEQ ID NO: 1 that codes for amino acid sequences represented by SEQ ID NO: 2. The estB gene is composed of a nucleotide sequence represented by SEQ ID NO: 3 that codes for amino acid sequences represented by SEQ ID NO: 4.

The eltAB gene was amplified using a polymerase chain reaction (PCR). Two primers were synthesized for this reaction:
- a synthetic DNA oligonucleotide designated "LT-F", which is composed of a nucleotide sequence represented by SEQ ID NO: 5 and
- a synthetic DNA primer designed "LT-R", which is composed of a nucleotide sequence represented by SEQ ID NO: 6.

The PCR was performed in a BIORAD PTC-100 thermal cycler (BIORAD, CA) in 50 µl reaction volume containing 1× pfu DNA polymerase buffer (with $Mg^{++}$), 0.2 mM dNTP, 0.5 µM each of LT-F and LT-R, 1 µl stock solution of genomic DNA from field isolate 3030-2, and one unit of pfu DNA polymerase (Strategene, CA). The PCR program contained one cycle of 2 minutes at 94° C.; 30 cycles of 30 seconds at 94° C., 30 seconds at 55° C., and 2 minutes at 72° C.; followed by an extension of 6 minutes at 72° C.

The amplified eltAB gene (i.e., the reaction product from the PCR) was verified to be the correct size using agarose gel electrophoresis, and then excised from the gel and purified using QIAquick Gel Extraction Kit (commercially available from QIAGEN, CA). The purified eltAB gene PCR product was then eluted in 35 µl $ddH_2O$.

The eltAB gene was cloned into a pBR322 plasmid vector (commercially available from Promega, WI). The pBR322 vector was first digested with restriction enzyme EcoRV (commercially available from New England Biolab, MA) at 37° C. for 1 hour in a 25 µl reaction with 1× buffer (buffer 3 for EcoRV), 1×BSA, and 20 units of enzyme. After digestion, the digested pBR322 plasmid was purified by agarose gel electrophoresis using QIAquick Gel Extraction Kit (QIAGEN, CA). The digested pBR322 plasmid was then diluted into 35 µl of $ddH_2O$.

The cloning of the eltAB gene into vector pBR322 included a ligation reaction that was performed with T4 DNA Ligase (commercially available from New England Biolabs, MA) overnight at 16° C. in a reaction of 20 µl including 2 µl of 10× buffer, 1 µl of T4 ligase, 7 µl of the digested pBR322 stock solution and 10 µl of eltAB stock solution.

Two microliters of the T4 ligated product was introduced into 100 µl of *E. coli* competent cells from a porcine field isolate designated "field isolate 1836-2" using an ECM 630 (BTX®, CA) electroporator set to 2.5 kV, 25 uF of capacitance, and 200 ohms of resistance in a 0.1 cm gap electroporation cuvette (Sigma, MO). Field isolate 1836-2 is a nonpathogenic porcine *E. coli* field isolate that lacks the eltAB gene and the estB gene.

Field isolate 1836-2 was deposited on Jun. 6, 2008 under the terms of the Budapest Treaty with the American Type Culture Collection, 10801 University Blvd., Manassas, Va. 20110-2209, USA (ATCC®) and was given ATCC Patent Deposit Designation PTA-9260. All restrictions on the availability to the public of the deposited material will be irrevocably removed upon the granting of the patent, except for the requirements specified in 37 C.F.R. §1.808(b), and the term of the deposit will comply with 37 C.F.R. §1.806.

Strain 1836-2 expresses K88ac fimbria and colonizes the intestinal epithelium of K88-receptor positive pigs. 1836-2 strain alone does not cause disease in young pigs (Zhang et al., 2006, Significance of heat-stable and heat-labile enterotoxins in porcine colibacillosis in an additive model for pathogenicity studies, Infect. Immun. 74:3107-3114, the entire disclosure of which is herein incorporated by reference).

50 µl of the transformed 1836-2 cells were spread onto agar plates containing 50 µg/ml ampicillin. The plates were incubated overnight at 37° C.

Positive colonies (selected for ampicillin resistance) were observed on the plates. Plasmid DNA was extracted from positive colonies using kit QIAprep Spin Miniprep kit (QIAGEN, CA) and was screened by PCR initially and then sequenced with a BigDye Terminator Kit (commercially available from Applied Biosystem, CA) to ensure that the eltAB gene was inserted into pBR322 and stayed in a correct reading frame.

The resultant plasmid vector containing the eltAB gene was designated pLT and was purified (QIAprep Spin Miniprep kit, QIAGEN, CA) and diluted to a 0.1 µg/µl stock solution.

Example 2

Mutation of the eltAB Gene

The eltAB gene in pLT was mutated using site-directed mutagenesis so as to change the nucleotides corresponding to amino acid residue number 192 of the eltAB gene from 'AGA' to 'GGA'. The plasmid pLT was used as the template for producing a plasmid containing a sequence for this mutant, which was designated $pLT_{192}$.

To produce the $pLT_{192}$ mutant, two internal PCR primers were used:
- a synthetic DNA oligonucleotide designated "$LT_{192}$-F", which is composed of a nucleotide sequence represented by SEQ ID NO: 7 and
- a synthetic DNA oligonucleotide designated "$LT_{192}$-R", which is composed of a nucleotide sequence represented by SEQ ID NO: 8 in a PCR reaction. The PCR was performed in a BIORAD PTC-100 thermal cycler (BIORAD, CA) in 50 µl reaction volume containing 1 µl stock solution of pLT, 1× pfu DNA polymerase buffer (with $Mg^{++}$), 0.2 mM dNTP, 0.5 µM each of $LT_{192}$-F and $LT_{192}$-R, 1 ul pBR322 stock solution (100 ng/ul), and one unit of pfu DNA polymerase (Strategene, CA). The PCR program contained one cycle of 2 minutes at 94° C.; 30 cycles of 30 seconds at 94° C., 30 seconds at 55° C., and 2 minutes at 72° C.; followed by an extension of 6 minutes at 72° C.

The amplified mutated eltAB gene (i.e., the reaction product from the PCR) was verified to be the correct size using agarose gel electrophoresis, and then excised from the gel and purified using QIAquick Gel Extraction Kit (commercially available from QIAGEN, CA). The purified mutated eltAB gene PCR product was then eluted in 35 µl of $ddH_2O$.

Example 3

Cloning of the Mutated eltAB Gene

With the pLT plasmid as the DNA template, a portion of plasmid pBR322 and the 5' end of the eltAB gene was amplified using PCR primers to add an overhanging 5' end that will include a SfcI restriction site. The primers for this reaction included:
- a synthetic DNA oligonucleotide designated "pBREcoRI-F", which is composed of a nucleotide sequence represented by SEQ ID NO: 9 and
- $LT_{192}$-R.

The PCR was performed in a BIORAD PTC-100 thermal cycler (BIORAD, CA) in 50 µl reaction volume containing 1 µl stock solution of pLT, 1× pfu DNA polymerase buffer (with Mg++), 200 nM dNTP, 0.5 µM each of pBREcoRI-F and $LT_{192}$-R, and one unit of pfu DNA polymerase (Strategene, CA). The PCR program contained one cycle of 2 minutes at 94° C.; 30 cycles of 30 seconds at 94° C., 30 seconds at 55° C., and 2 minutes at 72° C.; followed by an extension of 6 minutes at 72° C.

The 3' end of the eltAB gene and a portion of plasmid pBR322 were also amplified using PCR primers to add an overhanging 3' end that has an EagI restriction site. The primers for this reaction included:

a synthetic DNA oligonucleotide designated "pBREagI-R", which is composed of a nucleotide sequence represented by SEQ ID NO: 10, and $LT_{192}$-F.

The PCR was performed in a BIORAD PTC-100 thermal cycler (BIORAD, CA) in 50 µl reaction volume containing 1 µl stock solution of pLT, 1× pfu DNA polymerase buffer (with Mg++), 0.2 mM dNTP, 0.5 µM each of $LT_{192}$-F and pBREagI-R, and one unit of pfu DNA polymerase (Strategene, CA). The PCR program contained one cycle of 2 minutes at 94° C.; 30 cycles of 30 seconds at 94° C., 30 seconds at 55° C., and 2 minutes at 72° C.; followed by an extension of 6 minutes at 72° C.

The amplified 5' and 3' end fragments of the mutated eltAB gene were purified (using kit QIAquick Gel Extraction, QIAGEN) and then connected in a SOE (splice overlap extension) PCR for the mutated porcine eltAB gene (coding $LT_{192}$ protein). The SOE PCR was performed in a reaction of 1× pfu DNA polymerase buffer (with Mg++), 0.2 mM dNTP, 20 µl of each purified 5' and 3' end PCR products, one unit of pfu polymerase and 0.5 unit of taq DNA polymerase (Applied Biosystem, CA). The SOE PCR program consisted of one cycle of 2 minutes at 94° C.; 10 cycles of 30 seconds at 94° C., 30 seconds at 45° C., and 3 minutes at 72° C.; followed by an extension of 10 minutes at 72° C.

This mutated eltAB gene ($LT_{192}$) was digested with restriction enzymes SfcI and EagI, so was the vector pBR322. Restriction enzyme digestion with SfcI and EagI restriction enzymes (New England Biolab, MA) was conducted at 37° C. for 1 hour in a 25 µl reaction with 1× buffer (buffer 3 for EagI and buffer 4 for SfcI), 1×BSA, and 20 units of enzyme. Digested products were purified by agarose gel electrophoresis using QIAquick Gel Extraction Kit (QIAGEN, CA), and ligated with T4 DNA Ligase (New England BioLab, MA) overnight at 16° C. in a reaction of 20 µl including 2 µl of 10× buffer, 1 µl of T4 ligase, 7 µl of vector and 10 µl of insert.

Two microliters of T4 ligated products were introduced into 100 µl of *E. coli* competent cells of 1836-2 in an electroporation using 2.5 kV, 25 uF of capacitance, and 200 ohms of resistance.

50 µl of the transformed 1836-2 cells were spread onto agar plates containing 50 µg/ml ampicillin. The plates were incubated overnight at 37° C.

Positive colonies (selected for ampicillin resistance) were observed on the plates. Plasmid DNA was extracted from positive colonies using kit QIAprep Spin Miniprep kit (QIAGEN, CA) and was screened by PCR initially and then sequenced with a BigDye Terminator Kit (commercially available from Applied Biosystem, CA). The resultant plasmid vector containing the mutated eltAB gene was designated pLT192 and was purified (QIAprep Spin Miniprep kit, QIAGEN, CA) and diluted to a 0.1 µg/µl stock solution.

Example 4

Generation of the Genetic Fusion of the Mutated eltAB Gene with the estB Gene

To generate a genetic fusion of the mutated eltAB gene with the estB gene, two PCR reactions were used. For the first, we designed two additional PCR primers:

a synthetic DNA oligonucleotide designated "STb:LT-F5", which is composed of a nucleotide sequence represented by SEQ ID NO: 11 and a synthetic DNA oligonucleotide designated "LT:STb-R4", which is composed of a nucleotide sequence represented by SEQ ID NO: 12.

The 'STb:LT-F5' forward primer contains nucleotides of the 3' end of the mutated eltAB gene, a Gly-Pro-Gly-Pro linker, and nucleotides of 5' end of the estB gene. The 'LT:STb-R4' reverse primer contains the 5' end of estB gene, the linker, and the 3' end of the mutated eltAB gene. A PCR using DNA templates from the plasmid $pLT_{192}$ and primers pBREcoRI-F and LT:STb-R4 amplified a portion of the pBR322 vector, the entire mutated eltAB gene (with its stop codon deleted), the Gly-Pro linker, and partial of the 5' end of the estB gene.

The first PCR was performed in a BIORAD PTC-100 thermal cycler (BIORAD, CA) in 50 µl reaction volume containing 1 µl stock solution of $pLT_{192}$, 1× pfu DNA polymerase buffer (with Mg++), 0.2 mM dNTP, 0.5 µM each of STb:LT-F5 and LT:STb-R4, and one unit of pfu DNA polymerase (Strategene, CA). The PCR program contained one cycle of 2 minutes at 94° C.; 30 cycles of 30 seconds at 94° C., 30 seconds at 55° C., and 2 minutes at 72° C.; followed by an extension of 6 minutes at 72° C.

A second PCR using genomic DNA from field isolate 3030-2 and PCR primers STb:LT-F5 and a synthetic DNA oligonucleotide designated "STbEagI-R", which is composed of a nucleotide sequence represented by SEQ ID NO: 13 amplified a portion of the 3' end of the mutated eltAB gene, the linker, and the estB gene. The PCR was performed in a BIORAD PTC-100 thermal cycler (BIORAD, CA) in 50 µl reaction volume containing 1 µl DNA stock solution of field isolate 3030-2, 1× pfu DNA polymerase buffer (with Mg++), 0.2 mM dNTP, 0.5 µM each of STb:LT-F5 and STbEagI-R, and one unit of pfu DNA polymerase (Strategene, CA). The PCR program contained one cycle of 2 minutes at 94° C.; 30 cycles of 30 seconds at 94° C., 30 seconds at 55° C., and 2 minutes at 72° C.; followed by an extension of 6 minutes at 72° C.

The amplified products were connected in a SOE PCR, and resulted in a fusion product of $LT_{192}$-Gly-Pro-linker-estB. The SOE PCR program consisted of one cycle of 2 minutes at 94° C.; 10 cycles of 30 seconds at 94° C., 30 seconds at 45° C., and 3 minutes at 72° C.; followed by an extension of 10 minutes at 72° C.

The amplified products were digested with restriction enzymes SfcI and EagI. Restriction enzyme digestion with SfcI and EagI restriction enzymes (New England Biolab, MA) was conducted at 37° C. for 1 hour in a 25 µl reaction with 1× buffer (buffer 3 for EagI and buffer 4 for SfcI), 1×BSA, and 20 units of enzyme. Digested products were purified by agarose gel electrophoresis using QIAquick Gel Extraction Kit (QIAGEN, CA), and ligated with T4 DNA Ligase (New England BioLab, MA) overnight at 16° C. in a reaction of 20 µl including 2 µl of 10× buffer, 1 µl of T4 ligase, 7 µl of the digested vector (pBR322) and 10 µl of the digested insert (amplified product).

Two microliters of T4 ligated products were introduced into 100 µl of *E. coli* competent cells of 1836-2 in an electroporation using 2.5 kV, 25 uF of capacitance, and 200 ohms of resistance.

50 µl of the transformed 1836-2 cells were spread onto agar plates containing 50 µg/ml ampicillin. The plates were incubated overnight at 37° C.

Positive colonies (selected for ampicillin resistance) were observed on the plates. Plasmid DNA was extracted from positive colonies using kit QIAprep Spin Miniprep kit (QIAGEN, CA) and was screened by PCR initially and then sequenced with a BigDye Terminator Kit (commercially available from Applied Biosystem, CA). The resultant plasmid vector containing the fusion of the mutated eltAB gene and the estB gene was designated "pLT$_{192}$:STb" and was purified (QIAprep Spin Miniprep kit, QIAGEN, CA) and diluted to a 0.1 µg/µl stock solution.

A stock of 1836-2 transformed with plasmid LT$_{192}$:STb (e.g., cultures of positive colonies) were maintained in 30% glycerol solution. This stock was designated vaccine strain "8488". Vaccine strain 8488 was deposited on Jun. 6, 2008 under the terms of the Budapest Treaty with the American Type Culture Collection, 10801 University Blvd., Manassas, Va. 20110-2209, USA (ATCC®) and was given ATCC Patent Deposit Designation PTA-9261. All restrictions on the availability to the public of the deposited material will be irrevocably removed upon the granting of the patent, except for the requirements specified in 37 C.F.R. §1.808(b), and the term of the deposit will comply with 37 C.F.R. §1.806.

Example 5

Alternatively, the first PCR reaction was replaced with the following to alter the "L-linker". For this example, two additional PCR primers containing the 'L-linker' (5'-cgagetcgg-tacccggggatc-'3, Clements and Cardenas, 1990, "Vaccines against enterotoxigenic bacterial pathogens based on hybrid Salmonella that express heterologous antigens", Res. Microbiol. 141:981-993, the entire disclosure of which is herein incorporated by reference) were designed to attempt to increase the flexibility between two proteins:
- a synthetic DNA oligonucleotide designated "LT:STb-R5", which is composed of a nucleotide sequence represented by SEQ ID NO: 14 and
- a synthetic DNA oligonucleotide designated "STb:LT$_B$-F", which is composed of a nucleotide sequence represented by SEQ ID NO: 15.

In a reaction similar to what is described in Example 4, a PCR using pBREcoRI-F and LT:STb-R5 and pLT$_{192}$:STb plasmid DNA amplified the mutated eltAB gene, the L-linker, and the 5' end of the estB gene, and then a second PCR (similar to the section PCR in Example 4) using STb:LTB-F and STbEagI-R amplified the 3' end of the mutated eltAB gene, the L-linker, and the estB gene. Two fragments were connected in a SOE PCR, digested with SfcI and EagI enzymes, and then ligated into vector pBR322.

Example 6

Vaccine Production and Administration

The vaccine was produced by incubating 25 µl of strain 8488 stock in 10 ml LB (Luria-Bertani) broth contain 50 µg/ml ampilicilin overnight at 37° C.

Three milliliters (3×10$^9$ colony-forming units or CFUs) of overnight-grown culture of strain 8488 was mixed within 219 ml of Esbilac milk replacer (Pet Ag, Inc., IA) for oral administration to pigs.

Piglets used in vaccine studies were delivered by C-section, randomly divided into three groups and raised in a gnotobiotic facility (germ-free environment). At the age of seven days, piglets were orally inoculated with normal flora bacteria including *Bacteriodes thetaiotaaomicron, Chlostridium clostridioforme, Lactobacillus brevis*, and *Escherichia coli* strain G58-1 to activate the naïve immune systems of these gnotobiotic piglets. These nonpathogenic bacteria are normally present in the intestines of pigs and part the normal flora. At the age of 14 days, pigs were arranged in three groups, a vaccine group and two negative controls. The first group of four pigs (in this and other examples hereafter known as the "Vaccine Strain" group) ingested the vaccine strain 8488 (in the milk replacer), the second group of four pigs (in this and other examples hereafter known as the "1836-2 (−)" group) ingested strain 1836-2 (3 milliliters or 3×10$^9$ CFUs of strain 1836-2 in 219 milliliters of milk replacer), and the third group of four pigs (in this and other examples hereafter known as the "Negative Control" group) ingested milk replacer alone.

One week later, pigs in the Vaccine Strain group were boosted with a second immunization with orally digestion of 3 ml of overnight-grown 8488 culture in 387 milliliters of milk replacer.

After another week, pigs in all three groups were challenged with 3 ml of overnight-grown culture of a wildtype pathogenic ETEC strain 3030-2 mixed in 387 milliliters of milk replacer. Pigs were under close observation for development of clinical symptoms including diarrhea and dehydration. 48 hours later, all pigs were subject of necropsy for histological examination. Blood samples were collected from each pig before and after each immunization, and before and after the challenge to monitor immunogenic response (see Example 11 for results). All pigs were observed to consume the inoculum and monitored for subsequent clinical signs, including vomiting, diarrhea, dehydration, and lethargy. At necropsy, small intestinal samples were collected at necropsy from each pig for bacterial colonization study.

Piglets were subjected to necropsy 48 hours post-inoculation after euthanasia, and samples of ileum (I) (3-5 cm proximal to the ileocecal valve), lower jejunum (LJ) (one-third to half of the distance between pyloric valve and ileocecal valve), upper jejunum (UJ) (half to two-thirds of the distance between pyloric valve and ileocecal valve), and duodenum (D) (3-5 cm distal to the pyloric valve) were collected for bacteriology and histopathology studies.

Example 8

Assessment of Piglet Dehydration

The level of dehydration following challenge was determined by measuring changes in blood packed cell volume (PCV) and plasma total protein (TP). Blood samples were drawn from each pig before and 18 h after inoculation, and tested for blood packed cell volume and plasma total protein as described elsewhere. Briefly, blood samples were placed in 75 mm capillary tubes and centrifuged for TP and PCV analysis. PCV was determined using a standard hematocrit total percentage chart. Plasma TP content was determined using a standard medical refractometer. An increase in PCV and plasma TP from pre-inoculation sample collection to post-inoculation sample collection served as an indication of dehydration.

Example 9

Assessment of Bacterial Intestinal Colonization

Determination of the magnitude and location of bacterial colonization of the small intestine was accomplished by quantitative culture and image analysis of immunohistochemically stained sections of piglet small intestine. The concentration of bacteria in CFU per gram of ileal tissue was determined. Briefly, ileal tissue was weighed, washed and ground in PBS (at the ratio of N gram tissue in 9×N ml of PBS), serially diluted, plated on blood agar (brain heart base) or LB agar plates, and incubated overnight at 37° C. after which bacterial colonies were enumerated.

Example 10

Piglet Brush Border Adherence Assay for the Assessment of K88 Receptor Expression Jejunum samples collected from each piglet at necropsy were used to prepare brush border vesicles following standard method. Small intestinal brush border vesicles from each piglet were tested for the adherence of *E. coli* expressing K88ab, K88ac, and K88ad fimbriae. Suspensions of bacteria mixed with brush borders were examined under phase contrast microscope for the adherence of bacteria to brush borders. The numbers of bacteria adhered to individual brush border vesicles were counted, and ten vesicles from each brush border sample were included for the bacteria calculation. Individual brush borders were considered adherent if there were more than 2 bacteria adhered to a brush border vesicle. Non-adherence pigs were excluded from the data analyses.

Example 11

Results

All pigs immunized with the 8488 vaccine strain (Vaccine Strain group) remained health, did not develop any diarrhea or dehydration after challenged with the porcine diarrheagenic ETEC strain 3030-2. The fecal water layer in the small intestines was 35.5% average (firm feces, normal, healthy). 100% protection was observed.

Pigs in the negative control groups (both the 1832-3 (−) and Negative Control groups) developed diarrhea after challenged with the porcine diarrheagenic ETEC strain 3030-2. The fecal water layer in the small intestine was greater than 90% (water accumulated in the small intestines, diarrhea).

Pigs in the vaccine group (Vaccine Strain group) were observed to have high anti-K88 and anti-LT antibodies, while those in the control groups (both the 1832-3 (−) and Negative Control groups) had no or significantly lower antibody detected (See Tables 1-6 below).

The small intestines of the pigs from the vaccine group (Vaccine Strain group) were largely colonized with the vaccine strain ($6.7 \times 10^8$ CFU/g), which prevented the colonization from the 3030-2 ($0$-$6 \times 10^4$ CFU/g); whereas the small intestines of the pigs from the negative control groups (both the 1832-3 (−) and Negative Control groups) were predominately colonized with the challenge 3030-2 strain ($1.03 \times 10^8$ CFU/g of 3030-2) which is the precondition for developing the diarrhea disease.

The presence of Anti-K88 antibodies and Anti-LT antibodies were measured using Western Blot analysis. The titers of Anti-K88 antibodies detected in blood serum for each group of pigs is presented in tables 1-3.

TABLE 1

Anti-K88 antibodies detected in blood serum (IgG titer).

| Anti-K88 IgG titer | 14-day (before immunization) | 28-day (before challenge) | 30-day (48 h post challenge) |
|---|---|---|---|
| Vaccine Strain | 0 | 1345 | 1600 |
| 1836-2 (—) | 0 | 475 | 400 |
| Negative Control | 0 | 113 | 134 |

TABLE 2

Anti-K88 antibodies detected in blood serum (IgM titer).

| Anti-K88 IgM titer | 14-day (before immunization) | 28-day (before challenge) | 30-day (48 h post challenge) |
|---|---|---|---|
| Vaccine strain | 0 | 2560 | 4305 |
| 1836-2 (—) | 0 | 452 | 905 |
| Negative control | 0 | 128 | 107 |

TABLE 3

Anti-K88 antibodies detected in blood serum (IgA titer).

| Anti-K88 IgA titer | 14-day (before immunization) | 28-day (before challenge) | 30-day (48 h post challenge) |
|---|---|---|---|
| Vaccine strain | 0 | 113 | 95 |
| 1836-2 (—) | 0 | 40 | 33.6 |
| Negative control | 0 | 1 | 1 |

The titers of Anti-LT antibodies detected in blood serum are presented in tables 4-6.

TABLE 4

Anti-LT antibodies detected in blood serum (IgG titer)

| Anti-LT IgG titer | 14-day (before immunization) | 28-day (before challenge) | 30-day (48 h post challenge) |
|---|---|---|---|
| Vaccine strain | 0 | 11.3 | 8 |
| 1836-2 (—) | 0 | 2.83 | 2.38 |
| Negative control | 0 | 1.4 | 1.4 |

TABLE 5

Anti-LT antibodies detected in blood serum (IgM titer)

| Anti-LT IgM titer | 14-day (before immunization) | 28-day (before challenge) | 30-day (48 h post challenge) |
|---|---|---|---|
| Vaccine strain | 0 | 5.7 | 9.5 |
| 1836-2 (—) | 0 | 6.7 | 4.8 |
| Negative control | 0 | 1.4 | 3.4 |

TABLE 5

Anti-LT antibodies detected in blood serum (IgA titer)

| Anti-LT IgA titer | 14-day (before immunization) | 28-day (before challenge) | 30-day (48 h post challenge) |
|---|---|---|---|
| Vaccine strain | 0 | 9.5 | 27 |
| 1836-2 (—) | 0 | 5.7 | 1 |
| Negative control | 0 | 3.4 | 1.4 |

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A live vaccine for porcine post-weaning diarrhea, comprising:
   an *Escherichia coli* strain producing K88 fimbria and a fusion protein including a mutant LT enterotoxin linked with a STb enterotoxin; and
   wherein the *Escherichia coli* strain is the strain deposited at the American Tissue Culture Collection under ATCC Patent Deposit Designation PTA-9261.

2. A vaccine against enterotoxigenic *Escherichia coli*, comprising:
   an *Escherichia coli* strain deposited at the American Tissue Culture Collection under ATCC Patent Deposit Designation PTA-9261.

* * * * *

SEQUENCE LISTING

<160> NUMBER OF SEQ ID NOS: 15

<210> SEQ ID NO 1
<211> LENGTH: 777
<212> TYPE: DNA
<213> ORGANISM: Escherichia coli

<400> SEQUENCE: 1

| | | | | | |
|---|---|---|---|---|---|
| atgaaaaata | taactttcat | ttttttattt | ttattagcat | cgccattata | tgcaaatggc | 60 |
| gacagattat | accgtgctga | ctctagaccc | ccagatgaaa | taaaacgttc | cggaggtctt | 120 |
| atgcccagag | ggcataatga | gtacttcgat | agaggaactc | aaatgaatat | taatctttat | 180 |
| gatcacgcga | gaggaacaca | aaccggcttt | gtcagatatg | atgacggata | tgtttccact | 240 |
| tctcttagtt | tgagaagtgc | tcacttagca | ggacagtata | tattatcagg | atattccact | 300 |
| tactatatat | atgttatagc | gacagcacca | aatatgttta | atgttaatga | tgtattaggc | 360 |
| gtatacagcc | ctcacccata | tgaacaggag | gtttctgcgt | taggtggaat | accatattct | 420 |
| cagatatatg | gatggtatcg | tgttaatttt | ggtgtgattg | atgaacgatt | acatcgtaac | 480 |
| agggaatata | gagaccggta | ttacagaaat | ctgaatatag | ctccggcaga | ggatggttac | 540 |
| agattagcag | gtttcccacc | ggatcaccaa | gcttggagag | aagaaccctg | gattcatcat | 600 |
| gcaccacaag | gttgtggaga | ttcatcagga | acaatcacag | gtgatacttg | taatgaggag | 660 |
| acccagaatc | tgagcacaat | atatctcagg | gaatatcaat | caaaagttaa | gaggcagata | 720 |
| ttttcagact | atcagtcaga | ggttgacata | tataacagaa | ttcgggatga | attatga | 777 |

<210> SEQ ID NO 2
<211> LENGTH: 254
<212> TYPE: PRT
<213> ORGANISM: Escherichia coli

<400> SEQUENCE: 2

Met Lys Asn Ile Thr Phe Ile Phe Phe Ile Leu Leu Ala Ser Pro Leu
1               5                   10                  15

Tyr Ala Asn Gly Asp Arg Leu Tyr Arg Ala Asp Ser Arg Pro Pro Asp
            20                  25                  30

Glu Ile Lys Arg Phe Arg Ser Leu Met Pro Arg Gly Asn Glu Tyr Phe
        35                  40                  45

Asp Arg Gly Thr Gln Met Asn Ile Asn Leu Tyr Asp His Ala Arg Gly
    50                  55                  60

Thr Gln Thr Gly Phe Val Arg Tyr Asp Asp Gly Tyr Val Ser Thr Ser
65                  70                  75                  80

Leu Ser Leu Arg Ser Ala His Leu Ala Gly Gln Tyr Ile Leu Ser Gly
                85                  90                  95

Tyr Ser Leu Thr Ile Tyr Ile Val Ile Ala Asn Met Phe Asn Val Asn
            100                 105                 110

Asp Val Ile Ser Val Tyr Ser Pro His Pro Tyr Glu Gln Glu Val Ser
        115                 120                 125

Ala Leu Gly Gly Ile Pro Tyr Ser Gln Ile Tyr Gly Trp Tyr Arg Val
    130                 135                 140

Asn Phe Gly Val Ile Asp Glu Arg Leu His Arg Asn Arg Glu Tyr Arg
145                 150                 155                 160

Asp Arg Tyr Tyr Arg Asn Leu Asn Ile Ala Pro Ala Glu Asp Gly Tyr
                165                 170                 175

```
Arg Leu Ala Gly Phe Pro Pro Asp His Gln Ala Trp Arg Glu Glu Pro
            180                 185                 190

Trp Ile His His Ala Pro Gln Gly Cys Gly Asp Ser Ser Arg Thr Ile
        195                 200                 205

Thr Gly Asp Thr Cys Asn Glu Glu Thr Gln Asn Leu Ser Thr Ile Tyr
    210                 215                 220

Leu Arg Glu Tyr Gln Ser Lys Val Lys Arg Gln Ile Phe Ser Asp Tyr
225                 230                 235                 240

Gln Ser Glu Val Asp Ile Tyr Asn Arg Ile Arg Asp Glu Leu
                245                 250

<210> SEQ ID NO 3
<211> LENGTH: 213
<212> TYPE: DNA
<213> ORGANISM: Escherichia coli

<400> SEQUENCE: 3
atgaaaaaga atatcgcatt tcttcttgca tctatgttcg ttttttctat tgctacaaat      60
gcctatgcat ctacacaatc aaataaaaaa gatctgtgtg aacattatag acaaatagcc     120
aaggaaagtt gtaaaaaagg ttttttaggg gttagagatg gtactgctgg agcatgtttt     180
ggcgcccaaa taatggttgc agcaaaagga tgc                                  213

<210> SEQ ID NO 4
<211> LENGTH: 71
<212> TYPE: PRT
<213> ORGANISM: Escherichia coli

<400> SEQUENCE: 4

Met Lys Lys Asn Ile Ala Phe Leu Leu Ala Ser Met Phe Val Phe Ser
1               5                   10                  15

Ile Ala Thr Asn Ala Tyr Ala Ser Thr Gln Ser Asn Lys Lys Asp Leu
            20                  25                  30

Cys Glu His Tyr Arg Gln Ile Ala Lys Glu Ser Cys Lys Lys Gly Phe
        35                  40                  45

Leu Gly Val Arg Asp Gly Thr Ala Gly Ala Cys Phe Gly Ala Gln Ile
    50                  55                  60

Met Val Ala Ala Lys Gly Cys
65                  70

<210> SEQ ID NO 5
<211> LENGTH: 26
<212> TYPE: DNA
<213> ORGANISM: Synthetic Oligonucleotide

<400> SEQUENCE: 5
atgattgaca tcatgttgca tatagg                                           26

<210> SEQ ID NO 6
<211> LENGTH: 21
<212> TYPE: DNA
<213> ORGANISM: Synthetic Oligonucleotide

<400> SEQUENCE: 6
cccctccagc ctagcttagt t                                                21

<210> SEQ ID NO 7
<211> LENGTH: 25
<212> TYPE: DNA
<213> ORGANISM: Synthetic Oligonucleotide
```

-continued

<400> SEQUENCE: 7
gattcatcag gaacaatcac aggtg                                      25

<210> SEQ ID NO 8
<211> LENGTH: 23
<212> TYPE: DNA
<213> ORGANISM: Synthetic Oligonucleotide

<400> SEQUENCE: 8
cctgtgattg ttcctgatga atc                                        23

<210> SEQ ID NO 9
<211> LENGTH: 22
<212> TYPE: DNA
<213> ORGANISM: Synthetic Oligonucleotide

<400> SEQUENCE: 9
ccacctgacg tctaagaaac ca                                         22

<210> SEQ ID NO 10
<211> LENGTH: 21
<212> TYPE: DNA
<213> ORGANISM: Synthetic Oligonucleotide

<400> SEQUENCE: 10
cggaagcgag aagaatcata a                                          21

<210> SEQ ID NO 11
<211> LENGTH: 46
<212> TYPE: DNA
<213> ORGANISM: Synthetic Oligonucleotide

<400> SEQUENCE: 11
gcaatcagtg ggccggggcc catgaaaaag aatatcgcat ttcttc               46

<210> SEQ ID NO 12
<211> LENGTH: 44
<212> TYPE: DNA
<213> ORGANISM: Synthetic Oligonucleotide

<400> SEQUENCE: 12 cttttcatg ggccccggcc cactgattgc cgcaattgaa ttgg                  44

<210> SEQ ID NO 13
<211> LENGTH: 29
<212> TYPE: DNA
<213> ORGANISM: Synthetic Oligonucleotide

<400> SEQUENCE: 13
gctgaatgct aattcggccg tatattagc                                  29

<210> SEQ ID NO 14
<211> LENGTH: 48
<212> TYPE: DNA
<213> ORGANISM: Synthetic Oligonucleotide

<400> SEQUENCE: 14
cgagctcggt acccggggat cgttttccat actgattgcc gcaattga             48

<210> SEQ ID NO 15
<211> LENGTH: 48
<212> TYPE: DNA

```
<400> SEQUENCE: 15
gatccccggg taccgagctc gaaaaagaat atcgcatttc ttcttgca         48
```